United States Patent [19]

Dubief et al.

[11] Patent Number: 5,627,148

[45] Date of Patent: May 6, 1997

[54] WASHING AND/OR CONDITIONING COMPOSITION FOR KERATINOUS MATERIALS BASED ON A SILICONE CONTAINING A HYDROXYACYLAMINO FUNCTIONAL GROUP AND ON SUBSTANTIVE POLYMERS

[76] Inventors: Claude Dubief, 9,rue Edmond Rostand, F-78150 Le Chesnay, France; Daniele Cauwet, 53,rue de Charonne, F-75011 Paris, France

[21] Appl. No.: 384,604

[22] Filed: Feb. 3, 1995

Related U.S. Application Data

[63] Continuation of Ser. No. 906,540, Jun. 30, 1992, abandoned.

[30] Foreign Application Priority Data

Jul. 4, 1991 [FR] France .................... 91 08388

[51] Int. Cl.$^6$ ...................................... C11D 1/90
[52] U.S. Cl. .................. 510/122; 510/123; 510/126
[58] Field of Search ............... 424/70.122; 252/174.15, 252/174.23, 8.6, 8.8, 8.9, DIG. 13, DIG. 2, 547

[56] References Cited

U.S. PATENT DOCUMENTS

| | | | |
|---|---|---|---|
| 4,349,532 | 9/1982 | Vanlerberghe et al. | 424/47 |
| 4,388,437 | 6/1983 | Ona | 524/588 |
| 4,529,586 | 7/1985 | De Marco et al. | 424/70 |
| 4,704,272 | 11/1987 | Oh et al. | 424/70 |
| 4,772,462 | 9/1988 | Boothe et al. | 424/70 |
| 4,915,938 | 4/1990 | Zawadzki | 424/70 |
| 4,978,561 | 12/1990 | Cray et al. | 427/387 |
| 5,151,210 | 9/1992 | Stenri et al. | 252/174.17 |
| 5,180,584 | 1/1993 | Sebag et al. | 424/401 |
| 5,275,755 | 1/1994 | Sebag et al. | 252/174.15 |
| 5,302,657 | 4/1994 | Hunh et al. | 524/588 |
| 5,449,475 | 9/1995 | Cauwet et al. | 252/174.23 |

FOREIGN PATENT DOCUMENTS

| | | |
|---|---|---|
| 0180464 | 10/1984 | European Pat. Off. . |
| 0180464 | 5/1986 | European Pat. Off. . |
| 342834 | 5/1989 | European Pat. Off. . |
| 0342834 | 11/1989 | European Pat. Off. . |
| 9208439 | of 0000 | France . |
| 2058103 | 8/1980 | United Kingdom . |

*Primary Examiner*—Paul Lieberman
*Assistant Examiner*—Michael P. Tierney
*Attorney, Agent, or Firm*—Brumbaugh, Graves, Donohue & Raymond

[57] ABSTRACT

Washing and/or conditioning composition for keratinous materials based on a silicone containing a hydroxyacylamino functional group and on substantive polymers.

The invention relates to a washing and/or conditioning composition for keratinous materials containing, in an aqueous medium suitable for these materials, at least one silicone containing a hydroxyacylamino functional group, at least one substantive polymer and at least one detergent surface-active agent.

18 Claims, No Drawings

WASHING AND/OR CONDITIONING COMPOSITION FOR KERATINOUS MATERIALS BASED ON A SILICONE CONTAINING A HYDROXYACYLAMINO FUNCTIONAL GROUP AND ON SUBSTANTIVE POLYMERS

This application is a continuation of application Ser. No. 07/906,540, filed on Jun. 30, 1992 now abandoned.

BACKGROUND OF THE INVENTION

The present invention relates to washing and/or conditioning compositions for keratinous materials, especially hair, based on a silicone containing a hydroxyacylamino functional group and on substantive polymers, as well as to processes for the treatment of these materials using such compositions.

It is well known that hair is sensitised or weakened to various degrees by the action of atmospheric agents such as the sun or bad weather as well as by the action of various cosmetic treatments such as permanent waves, hair straightenings, dyeings or bleachings. The hair then becomes difficult to disentangle and to style. Moreover, it is rough to the touch and lacks softness.

For this reason, washing and/or conditioning compositions for keratinous materials are looked for which would be able to confer, especially on fibres such as hair, good disentangling properties combined with good softness properties.

Shampooing compositions containing a substantive polymer have already been used in the past. These compositions are known to improve hair disentangling.

Shampooing compositions are also known containing silicones which generally give good softness properties to hair.

Moreover, compositions containing silicones and polymers, especially cationic polymers, are known.

However, these compositions were shown to be unsatisfactory in conferring all the desired disentangling and softening characteristics on the treated keratinous materials, especially on hair.

SUMMARY OF THE INVENTION

The Applicant has discovered, which is the subject of the invention, that the employment of a particular silicone containing a hydroxyacylamino functional group and of a substantive polymer in a surface-active detergent base led to disentangling and softness properties superior to those obtained with each of the constituents taken separately in the same base and at the total concentration of the combination.

Moreover, it was noted that this combination led to improved disentangling and softness properties, especially on hair, in relation to the properties which could be obtained with the combinations known in the state of the art.

These compositions, in their preferred embodiment, contain suspending agents, other than alcohols having 27 to 44 carbon atoms and containing one or two ether and/or thioether or sulphoxide groups.

The subject of the invention is thus a washing and/or conditioning composition for keratinous materials which contains at least one silicone with a hydroxyacylamino functional group, at least one substantive polymer, at least one surface-active detergent agent and optionally some suspending agents for silicones.

Another subject of the invention is a process for washing and/or conditioning keratinous materials, in particular hair, using such a composition.

Other subjects of the invention will appear in the course of the description and the examples which follow.

DETAILED DESCRIPTION OF THE INVENTION

The washing and/or conditioning composition for keratinous materials, in accordance with the invention, is essentially characterised in that it contains, in an aqueous medium, at least one silicone containing a hydroxyacylamino functional group, at least one substantive polymer and at least one surface-active agent having detergent properties.

The silicone containing a hydroxyacylamino functional group is chosen especially from the compounds corresponding to the formula:

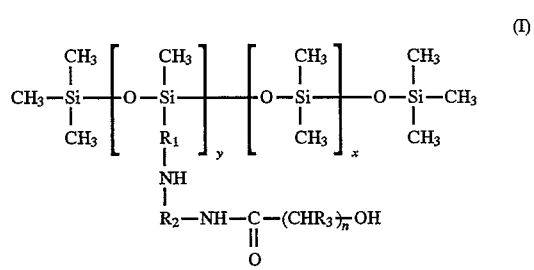

(I)

in which:

$R_1$ and $R_2$ denote $(CH_2)$, $(CH_2)_3$, $(CH_2)_4$ or $-CH_2CH(CH_3)CH_2-$;

$R_3$ denotes hydrogen, hydroxyl, alkyl or hydroxyalkyl;

n is an integer varying from 2 to 7;

x is an integer varying from 20 to approximately 1,500;

y varies between approximately 0.5 and 10;

and the y/x ratio is less than 0.05.

Such silicones are more particularly described in European Patent Application EP-A-0342834.

A more particularly preferred silicone of the formula (I) is that corresponding to formula (I), in which:

$R_1$ denotes $-CH_2CH(CH_3)CH_2-$;

$R_2$ denotes $-(CH_2)_2-$;

$R_3$ denotes hydrogen;

x is equal to 392;

y is equal to 8;

n is equal to 3.

Such silicones are sold in particular under the name Q2-8413 by the Company Dow Corning.

The silicones containing a hydroxyacylamino function group are present in the compositions in accordance with the invention in proportions preferably of between 0.1 and 20% by weight, and in particular between 0.5 and 10% by weight in relation to the total weight of the composition.

A "substantive polymer" means a polymer which can be made visible with the help of the acid dye Red 80 according to Richard J. Crawford, Journal of the Society of Cosmetic Chemists, 1980 31 (5), pages 273 to 278.

The substantive polymers are chosen in particular from polymers containing primary, secondary, tertiary and/or quaternary amine groups which form part of the polymer chain or are directly connected to the latter and which have a molecular weight of between 500 and approximately 5,000,000 and preferably between 1,000 and 3,000,000 and are different from the copolymer of diallyldialkylammonium and of an anionic monomer such as acrylic acid.

Among these polymers there may be mentioned more particularly the quaternised proteins and the polymers of the polyamine, polyaminoamide and quaternarypolyammonium class.

A. The quaternised proteins are in particular polypeptides which are chemically modified and which carry quaternary ammonium groups at the chain end or grafted on the latter:

collagenhydrolysates carrying triethylammonium groups such as the products sold under the name "Quat-Pro E" by the Company Maybrook and called, in the CTFA dictionary, "Triethonium Hydrolyzed Collagen Ethosulfate";

collagen hydrolysates carrying trimethylammonium or dimethylstearylammoniumchloride groups, sold under the name "Quat-Pro S" by the Company Maybrook and called, in the CTFA dictionary, "Steartrimonium Hydrolyzed Collagen";

animal protein hydrolysates carrying dimethylbenzylammonium groups such as the products sold under the name "Crotein BTA" by the Company Croda and called, in the CTFA dictionary, "Benzyltrimonium Hydrolyzed Animal Protein";

protein hydrolysates carrying, on the polypeptide chain, quaternary ammonium groups containing at least one alkyl radical having from 1 to 18 carbon atoms.

Among these protein hydrolysates, there may be mentioned among others:

Croquat L, in which the polypeptide chain has an average molecular weight of approximately 2,500 and in which the quaternary ammonium group contains a $C_{12}$ alkyl group;

Croquat M, in which the polypeptide chain has an average molecular weight of approximately 2,500 and in which the quaternary ammonium group contains a $C_{10}$–$C_{18}$ alkyl group;

Croquat S, in which the polypeptide chain has an average molecular weight of approximately 2,700 and in which the quaternary ammonium group contains a $C_{18}$ alkyl group;

Croquat Q, in which the polypeptide chain has an average molecular weight of the order of 12,000 and in which the quaternaryammonium group contains at least one alkyl group having from 1 to 18 carbon atoms;

a quaternised vegetable protein from soya sold under the name Croquat Soya.

These various products are sold by the Company Croda.

a quaternised protein resulting from the condensation of cocamidopropyldimethylamine with a hydrolysed animal protein, called, in the supplement to the 3rd edition (1982) of the CTFA dictionary, Cocamidopropyldimonium Hydroxypropylamino Hydrolysed Animal Protein, sold under the name Lexein QX 3000 by the Company Inolex.

B. The polymers of the polyamine, polyaminoamide or quaternary polyammonium class, which can be used in accordance with the present invention, are described in particular in the French Patents of the Applicant No. 2,505,348 or 2,542,997.

Among these polymers, there may be mentioned:

(1) optionally quaternised vinylpyrrolidone/dialkylaminoalkyl acrylate or methacrylate copolymers, such as the products sold under the name "Gafquat" by the Company Gaf Corporation, such as, for example, "Gafquat 734 or 755", or else the products called "Copolymer 845, 958 and 937". These polymers are described in detail in French Patents 2,077,143 and 2,393,573.

(2) Cellulose ether derivatives containing quaternary ammonium groups described in French Patent 1,492,597 and in particular the polymers marketed under the names "JR" (JR 400, JR 125, JR 30M) or "LR" (LR 400, LR 30M) by the Company Union Carbide Corporation. The polymers are also defined in the CTFA dictionary as quaternary ammoniums of hydroxyethyl cellulose which has reacted with an epoxide substituted with a trimethylammonium group.

(3) Cationic cellulose derivatives such as the copolymers of cellulose or cellulose derivatives grafted with a water-soluble quaternary ammonium monomer and described in greater detail in American Patent 4,131,576, such as the hydroxyalkyl celluloses such as hydroxymethyl, hydroxyethyl or hydroxypropyl cellulose grafted with a methacryloylethyltrimethylammonium, methacrylamidopropyltrimethylammonium or dimethyldiallylammonium salt.

The marketed products which correspond to this definition are more particularly the products sold under the names "Celquat L 200" and "Celquat H 100" by the Company National Starch.

(4) The quaternised polysaccharides desribed more particularly in American Patents 3,589,578 and 4,031,307 and more particularly the product marketed under the name "Jaguar C 13 S" and sold by the Company Meyhall.

(5) Polymers consisting of piperazinyl units and of divalent, straight- or branched-chain alkylene or hydroxyalkylene radicals, optionally interrupted by oxygen, sulphur or nitrogen atoms or by aromatic or heterocyclic rings, as well as the oxidation and/or quaternisation products of these polymers. Such polymers are described in French Patents 2,162,025 and 2,280,361.

(6) Water-soluble polyaminoamides prepared in particular by polycondensation of an acid compound with a polyamine. These polyaminoamides can be crosslinked by an epihalohydrin, a diepoxide, a dianhydride, an unsaturated anhydride, a bisunsaturated derivative, a bishalohydrin, a bisazetidinium, a bishaloacyldiamine, an alkyl bishalide or by an oligomer resulting from the reaction of a bifunctional compound reactive with respect to a bishalohydrin, a bisazetidinium, a bishaloacyldiamine, an alkyl bishalide, an epihalohydrin, a diepoxide or a bisunsaturated derivative; the crosslinking agent being used in proportions ranging from 0.025 to 0.35 mol per amine group of the polyaminoamide.

These polyaminopolyamides can be alkylated or, if they contain one or more tertiary amine functional groups, quaternised. Such polymers are described in particular in French Patents 2,252,840 and 2,368,508.

(7) Polyaminoamide derivatives resulting from the condensation of polyalkylenepolyamines with polycarboxylic acids followed by an alkylation by bifunctional agents. There may be mentioned, for example, the adipic acid-dialkylaminohydroxyalkyldialkylenetriamine polymers in which the alkyl radical contains 1 to 4 carbon atoms and preferably denotes methyl, ethyl or propyl. Such polymers are described in French Patent 1,583,363.

Among these derivatives, there may be more particularly mentioned the adipic acid/dimethylaminohydroxypropyl/diethylenetriamine polymers sold under the names "Cartaretine F, $F_4$ or $F_8$" by the Company Sandoz.

(8) Polymers obtained by reaction of a polyalkylenepolyamine containing two primaryamine groups and at least one secondary amine group with a dicarboxylic acid chosen from diglycolic acid and saturated aliphatic dicarboxylic acids having from 3 to 8 carbon atoms. The molar ratio of polyalkylenepolyamine to dicarboxylic acid being between 0.8:1 and 1.4:1; the polyaminoamide resulting therefrom being brought to reaction with epichlorohydrin in a molar ratio of epichlorohydrin in relation to the secondary amine group of the polyaminoamide of between 0.5:1 and 1.8:1. Such polymers are described in particular in American Patents 3,227,615 and 2,961,347.

Polymers of this type are in particular marketed under the name "Hercosett 57" by the Company Hercules Incorporated or else under the name of "PD 170" or "Delsette 101" by the Company Hercules in the case of the adipic acid/epoxypropyl/diethylenetriamine copolymer.

(9) Cyclopolymers having a molecular weight of 20,000 to 3,000,000 such as the homopolymers containing, as principal constituent of the chain, units corresponding to the formulae (II) or (II'):

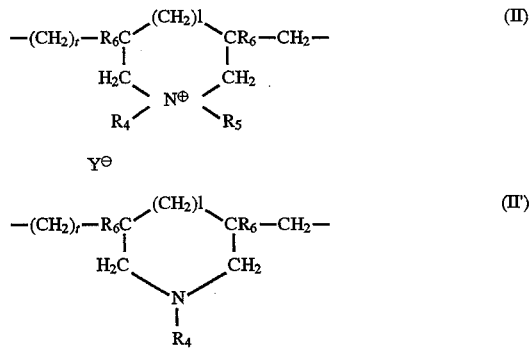

1 and t are equal to 0 or 1, and the sum 1+t=1;

$R_6$ denotes hydrogen or methyl;

$R_4$ and $R_5$ denote, independently of each other, an alkyl group having from 1 to 22 carbon atoms, a hydroxyalkyl group in which the alkyl group preferably has 1 to 5 carbon atoms or a lower amidoalkyl group and where $R_4$ and $R_5$ can denote, Jointly with the nitrogen atom to which they are connected, heterocyclic groups such as piperidinyl or morpholinyl, as well as copolymers containing units of formulae (II) or (II') and units derived from acrylamide or from diacetoneacrylamide;

$Y^\ominus$ is an anion such as bromide, chloride, acetate, borate, citrate, tartrate, bisulphate, bisulphite, sulphate or phosphate.

Among the polymers defined above, there may be more particularly mentioned the homopolymer of dimethyldiallylammonium chloride sold under the name "Merquat 100", which has a molecular weight of less than 100,000, or the copolymer of dimethyldiallylammonium chloride and of acrylamide which has a molecular weight of greater than 500,000 and is sold under the name "Merquat 550" by the Company Merck.

These polymers are described more particularly in French Patent 2,080,759 and its Certificate of Addition No. 2,190,406.

(10) The polymer of quaternary polyammonium containing repeat units corresponding to the formula:

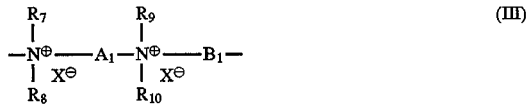

in which $R_7$ and $R_8$, $R_9$ and $R_{10}$, being identical or different, represent aliphatic, alicyclic or arylaliphatic radicals containing 1 to 20 carbon atoms or lower hydroxyalkylaliphatic radicals or else $R_7$ and $R_8$ and $R_9$ and $R_{10}$, together or separately, form, with the nitrogen atoms to which they are connected, heterocycles which optionally contain a second hetero atom other than nitrogen or else $R_7$, $R_8$, $R_9$ and $R_{10}$ represent a linear or branched $C_1$-$C_6$ alkyl radical substituted with a nitrile, ester, acyl, amide or

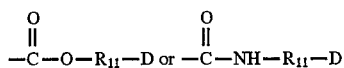

group, where $R_{11}$ is an alkylene and D a quaternary ammonium group.

$A_1$ and $B_1$ represent polymethylene groups containing from 2 to 20 carbon atoms, which may be linear or branched, saturated or unsaturated, and which may contain, connected to or inserted into the principal chain, one or more aromatic rings or one or more oxygen or sulphur atoms or sulphoxide, sulphone, disulphide, amino, alkylamino, hydroxyl, quaternary ammonium, ureido, amide or ester groups, and $X^\ominus$ denotes an anion derived from an inorganic or organic acid.

$A_1$ and $R_7$ and $R_9$ may form, with the two nitrogen atoms to which they are connected, a piperazine ring; additionally, if $A_1$ denotes a linear or branched, saturated or unsaturated alkylene or hydroxyalkylene radical, $B_1$ may also denote a group:

$$(CH_2)_n-CO-D-OC-(CH_2)_n-$$

which D denotes:

a) a glycol residue of formula: —O—Z—O— where Z denotes a linear or branched hydrocarbon radical or a group corresponding to the formulae:

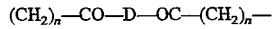

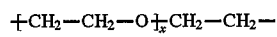

where x and y denote an integer from 1 to 4, representing a defined and single degree of polymerisation or any number whatever from 1 to 4 representing an average degree of polymerisation;

b) a bis-secondary diamine residue such as a piperazine derivative;

c) a bisprimary diamine residue of formula:

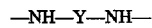

where Y denotes a linear or branched hydrocarbon radical, or else the bivalent radical $$-CH_2-CH_2-S-S-CH_2-CH_2-$$

d) a ureylene group of formula:

$$-NH-CO-NH-;$$

$X^\ominus$ is an anion such as choride or bromide.

These polymers have a molecular mass generally of between 1,000 and 100,000.

Polymers of this type are described in particular in French Patents 2,320,330, 2,270,846, 2,316,271, 2,336,434 and 2,413,907 and the U.S. Pat. Nos. 2,273,780, 2,375,853, 2,388,614, 2,454,547, 3,206,462, 2,261,002, 2,271,378, 3,874,870, 4,001,432, 3,929,990, 3,966,904, 4,005,193, 4,025,617, 4,025,627, 4,025,653, 4,026,945 and 4,027,020.

(11) Polymers of quaternary polyammonium consisting of units of formula:

$$-\overset{R_{12}}{\underset{\underset{R_{13}}{|}}{N^{\oplus}}}-(CH_2)_{\overline{x}}NH-\overset{O}{\overset{\|}{C}}-(CH_2)_{\overline{m}}\overset{O}{\overset{\|}{C}}-NH-(CH_2)_{\overline{y}}\overset{R_{14}}{\underset{\underset{R_{15}}{|}}{N^{\oplus}}}-A- \quad (IV)$$
$$X^{\ominus} \qquad X^{\ominus}$$

in which:

$R_{12}$, $R_{13}$, $R_{14}$ and $R_{15}$, which are identical or different, represent a hydrogen atom or a methyl, ethyl, propyl, β-hydroxyethyl, β-hydroxypropyl or —$CH_2CH_2$($OCH_2CH_2$)$_p$OH radical, where p is equal to 0 or an integer of between 1 and 6, with the proviso that $R_{12}$, $R_{13}$, $R_{14}$ and $R_{15}$ do not simultaneously represent a hydrogen atom;

x and y, which are identical or different, are integers of between 1 and 6;

m is equal to 0 or to an integer of between 1 and 34;

x denotes a halogen atom;

A denotes a dihalide radical and preferably represents

—$CH_2$—$CH_2$—O—$CH_2$—$CH_2$—

Such compounds are described in more detail in the Application EP-A-122,324.

It is possible, for example, to mention among the latter the products "Mirapol A 15", "Mirapol AD1", "Mirapol AZ1", "Mirapol 175", sold by the Company Miranol.

(12) Homopolymers or copolymers derived from acrylic or methacrylic esters or amides and containing the units:

$$-CH_2-\overset{R_{18}}{\underset{|}{C}}-\overset{|}{\underset{|}{C=O}}-\overset{|}{\underset{|}{O}}-\overset{|}{\underset{\overset{|}{N}}{A_2}}, \quad -CH_2-\overset{R_{18}}{\underset{|}{C}}-\overset{|}{\underset{|}{C=O}}-\overset{|}{\underset{|}{O}}-\overset{|}{\underset{|}{A_2}}-\overset{|}{\underset{X^{\ominus}_2}{N^{\oplus}-R_{21}}} \text{ or } -CH_2-\overset{R_{18}}{\underset{|}{C}}-\overset{|}{\underset{|}{C=O}}-\overset{|}{\underset{|}{NH}}-\overset{|}{\underset{|}{A_2}}-\overset{R_{19}-\underset{|}{N^{\oplus}}-R_{21}}{\underset{R_{20} \quad X^{\ominus}_2}{}} \quad (V)$$

in which:

$R_{18}$ denotes H or $CH_3$;

$A_2$ is a linear or branched alkyl group of 1 to 6 carbon atoms or a hydroxyalkyl group of 1 to 4 carbon atoms;

$R_{19}$, $R_{20}$ and $R_{21}$, which are identical or different, represent an alkyl group having from 1 to 18 carbon atoms or a benzyl radical;

$R_{16}$ and $R_{17}$ represent hydrogen or an alkyl group having from 1 to 6 carbon atoms;

$X^{\ominus}_2$ denotes a methosulphate anion or a halide such as chloride or bromide.

The comonomer(s) which may be used belong(s) to the class of acrylamide, methacrylamide, diacetone acrylamide, acrylamide and methacrylamide substituted at the nitrogen by lower alkyls, acrylic or methacrylic acids or their esters, vinylpyrrolidone or vinyl esters.

Among these compounds, there may be mentioned the copolymer of acrylamide and of dimethylaminoethyl methacrylate quaternised with dimethyl sulphate and sold under the name "Hercofloc" by the Company Hercules, the copolymer of acrylamide and of methacryloyloxyethyltrimethylammonium chloride—described in the Patent Application EP-A-80976—and sold under the name "Bina Qat P100" by the Company Ciba Geigy, or again the poly (methacrylamidopropyltrimethylammoniumchloride) sold under the name "Polymaptac" by the Company Texaco Chemicals or methacryloyloxyethyltrimethylammonium methosulphate and its copolymer with acrylamide sold under the name "Reten" by the Company Hercules.

(13) Quaternary polymers of vinylpyrrolidone and of vinylimidazole such as, for example, the products marketed under the names "Luviquat FC 905, FC 550 and FC 370" by the Company BASF.

(14) Polyamines such as Polyquart H sold by Henkel, referenced under the name "Polyethylene Glycol (15) Tallow Polyamine" in the CTFA dictionary.

Other substantive polymers which can be used in accordance with the invention are polyalkyleneimines, in particular polyethyleneimines, polymers containing vinylpyridine or vinylpyridinium units, condensates of polyamines and of epichlorohydrin, quaternary polyureylenes and chitin derivatives.

It is also possible to mention polymers derived from chitosan, chosen in particular from those described in French Patent 2,137,684 and containing units corresponding to the formulae (VI):

$$\text{(VI)}$$

(A) unit with $CH_2OH$, OH, H, NHCOCH$_3$ substituents (B) unit with $CH_2OH$, OH, H, NH$_2$ substituents (C) unit with $CH_2OH$, OH, H, NH—CO—R—COOH substituents The unit (A) is present in proportions of 0 to 30%, the unit (B) of 5 to 50%, the unit (C) of 30 to 90% by weight. R represents a linear or branched alkylene group containing from 2 to 5 carbon atoms.

The preferred polymer contains preferably 0 to 20% of unit (A), 40 to 50% of unit (B) and 40 to 50% of 5 unit (C) in which R denotes an alkylene radical and preferably —$CH_2$—$CH_2$—.

Such a polymer will be denoted in the examples by "polymer P1".

The particularly preferred polymers in the compositions in accordance with the invention are the following:

the block copolymer containing units of formula:

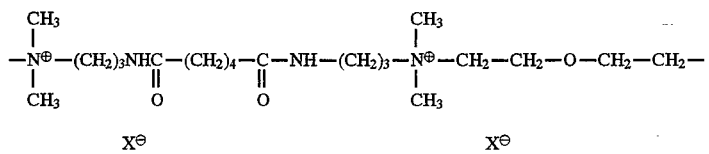

and of formula:

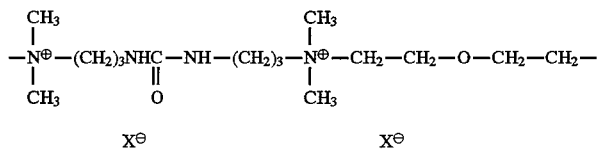

$X^{\ominus}$ is a halide, sold under the name "Mirapol 175" by the Company Miranol.

the cyclopolymers of dimethyldiallylammonium sold under the names "Merquat 100", "Merquat 550" by the Company Merck;

chitosan derivatives.

The substantive polymers which may be used in accordance with the invention are present in the compositions in proportions of between 0.05 and 8% by weight and preferably between 0.1 and 5% by weight in relation to the total weight of the composition.

When the compositions are used as washing compositions, they contain detergent surface-active agents chosen in particular from the anionic, amphoteric, zwitterionic or nonionic surface-active agents or their mixtures.

Among the anionic surface-active agents, there may be mentioned the alkali metal salts, the ammonium salts, the amine salts, the aminoalcohol salts or the magnesium salts of the following compounds: the alkyl ether sulphates, alkylamidoether sulphates, alkylarylpolyether sulphates or monoglyceride sulphates; the alkylsulphonates, alkylamidesulphonates, alkylarylsulphonates, olefinsulphonates or paraffinsulphonates; the alkylsulphosuccinates, the alkylethersulphosuccinates or the alkylamidesulphosuccinates; the alkylsulphosuccinamates; the alkylsulphoacetates; the alkyl ether phosphates; the acylsarcosinates or the N-acyltaurates.

The alkyl or acyl radical of these various compounds generally consists of a carbon chain containing from 12 to 20 carbon atoms.

Among the anionic surface-active agents, there may also be mentioned the fatty acid salts such as the salts of oleic, ricinoleic, palmitic or stearic acid; the acids of copra oil or of hydrogenated copra oil; the acyl lactylates, the acyl radical of which contains from 8 to 20 carbon atoms.

It is also possible to use weakly anionic surface-active agents, such as the polyoxyalkylenated carboxylic acid ethers, in particular those containing 2 to 50 ethylene oxide groups.

The nonionic surface-active agents are more particularly chosen from the alcohols or the α-diols or the alkylphenols or the polyethoxylated, polypropoxylated or polyglycerolated fatty acids, with a fatty chain containing 8 to 18 carbon atoms, the number of ethylene oxide or propylene oxide groups being between 2 and 50 and the number of glycerol groups being between 2 and 30.

It is also possible to mention the copolymers of ethylene oxide and of propylene oxide; the condensates of ethylene oxide and of propylene oxide with fatty alcohols; the polyethoxylated fattyamides having preferably 2 to 30 mol of ethylene oxide; the polyglycerolated fatty amides containing preferably 1 to 5 glycerol groups and in particular 1.5 to 4; the polyethoxylated fatty amines having preferably 2 to 30 mol of ethylene oxide; the oxyethylenated fatty acid esters of sorbitan having preferably 2 to 30 mol of ethylene oxide; the fatty acid esters of sucrose, the fatty acid esters of polyethylene glycol, the fatty acid esters of glycols, the alkylpolyglycosides, the amine oxides such as the oxides of ($C_{10}$–$C_{14}$)alkylamines or of N-acylamidopropylmorpholine.

The preferred amphoteric or zwitterionic surface-active agents are the derivatives of secondary or tertiaryaliphatic amines, in which the aliphatic radical is a linear or branched chain containing 8 to 18 carbon atoms and which contains at least one water-solubilising carboxylate, sulphonate, sulphate, phosphate or phosphonate anionic group; the ($C_8$–$C_{20}$)alkylbetaines, the sulphobetaines, the ($C_8$–$C_{20}$) alkylamido($C_1$–$C_6$)alkylbetaines or the ($C_8$–$C_{20}$)alkylamido ($C_1$–$C_6$)alkylsulphobetaines.

Among the amine derivatives, there may be mentioned the products sold under the name "Miranol", such as described in the Patents U.S. Pat. Nos. 2,528,378 and 2,781,354 and listed in the CTFA dictionary, 3rd edition, 1982, under the name of Amphocarboxyglycinates and Amphocarboxypropionates.

The surface-active agents are used in the compositions in accordance with the invention in sufficient proportions to confer a detergent character on the composition and comprise preferably between 5 and 50% by weight in relation to the total weight of the composition and in particular between 8 and 35%.

The compositions in accordance with the invention generally have a pH of between 2 and 9 and in particular between 3 and 8.

The aqueous medium may consist solely of water or of a mixture of water and of a cosmetically acceptable solvent, such as a $C_1$–$C_4$ lower alcohol such as ethanol, isopropanol or n-butanol or the alkylene glycols such as ethylene glycol or the glycol ethers.

The compositions in accordance with the invention may also contain as a preferred embodiment suspending agents, other than alcohols having 27 to 44 carbon atoms and containing one or two ether and/or thioether or sulphoxide groups.

Among these agents, there may be mentioned:

a) the compounds of formula:

$$R_{22}X \qquad (III)$$

in which $R_{22}$ is an aliphatic radical containing a long carbon chain, optionally interrupted by oxygen atoms, and X is a carboxylic, sulphuric or phosphoric acid residue or a radical derived from a carboxylic acid or from an amide; these compounds of formula (III) are chosen from those in which:

(i) $R_{22}$ is a $C_{11}-C_{21}$ alkyl or alkenyl radical and X is:

a group COOD where D is a mono- or polyhydroxyalkyl radical derived from a $C_2-C_3$ polyol or a $CH_2CH_2SO_3M$ radical, a group $CO(OCH_2CH_2)_n$—OH where n has a value of between 2 and 150, a group

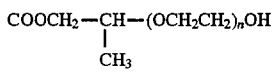

where n has a value of between 2 and 150, it being possible to esterify the free OH functional groups of the groups defined above with an acid $R_{22}COOH$ where $R_{22}$ is a $C_{11}-C_{21}$ alkyl or alkenyl, a group $CONR_{23}R_{24}$ where $R_{23}$ and $R_{24}$ represent hydrogen or $C_1-C_4$ hydroxyalkyl, one at least representing $C_1-C_4$ hydroxyalkyl, a group $OSO_3M$ or $\frac{1}{3} PO_4^{3-}M_3$ where M represents an alkali metal, ammonium or a $C_1-C_4$ alkanolamine residue.

(ii) $R_{22}$ denotes a radical $R_{25}(OC_2H_4)_l\ OCH_2$ and X denotes a group COOM where M has the meaning shown above, $R_{25}$ denoting a $C_{12}-C_{14}$ alkyl radical and l an integer or decimal number of between 2.5 and 10, or else $R_{25}$ denotes oleyl and l varies from 2 to 9 or again $R_{25}$ denotes $(C_8-C_9)$ alkylphenyl and l varies from 4 to 8, or the derivatives in which $R_{22}$ denotes a $(C_{12}-C_{16})$ alkyl ether group and X a group $CONR_{23}R_{24}$, in which $R_{23}$ and $R_{24}$ have the same meaning as that shown above;

b) dimethyl($C_{16}-C_{22}$) alkylamine oxides;

c) biopolysaccharides chosen, for example, from xanthan gums and scleroglucans.

These suspending agents are used in the compositions in accordance with the invention in proportions generally of between 0.1 and 20% by weight and preferably between 0.5 and 10% by weight in relation to the total weight of the composition.

The compositions in accordance with the invention can also contain pearlescence or opacifying agents in proportions which can range to up to 3%, such as sodium or potassium palmitates, sodium or potassium stearates or hydroxystearates or ethylene glycol mono- or distearate.

These compositions can also contain viscosity regulating agents, such as electrolytes such as sodium chloride or sodium xylenesulphonate, hydrotropes, thickeners such as cellulose derivatives, such as, for example, carboxymethyl cellulose, hydroxypropyl cellulose, hydroxyethyl cellulose, guar gum or hydroxypropylated guar gums.

These viscosity regulating agents are used in proportions which can range to up to 10% by weight in relation to the total weight of the composition and preferably are less than 5% by weight.

The compositions can also contain other agents which have the effect of improving the cosmetic properties of the hair and/or of the skin, with the proviso that they do not change the stability of the compositions, among which there may be mentioned cationic surface-active agents, polymers or proteins other than quaternised proteins, oils, waxes, resins or silicone gums other than the silicone derivatives defined above.

The polymers, cationic surface-active agents, nonguaternised proteins and silicones other than the silicones containing a hydroxyacylamino group of formula (I) are preferably used in proportions of between 0.05 and 6%, and in particular between 0.1 and 3% by weight in relation to the total weight of the composition.

These compositions can contain any other adjuvants normally used in cosmetics and especially in the treatment of the hair and/or of the skin, such as fragrances, preservatives, sequestering agents, foam stabilisers, propellants, sunscreens, dyes, acidifying or alkalinising agents or other adjuvants according to the use envisaged.

The process for washing and/or conditioning keratinous materials such as the hair and/or the skin, consists in applying, to these damp materials, any one of the compositions defined above and in proceeding, preferably, to a rinsing after their application.

The following examples are intended to illustrate the invention without being of a limiting nature.

EXAMPLE 1

A shampoo of the following composition is prepared:

| | |
|---|---|
| Surface-active agent of the polyoxyethylenated carboxylic acid ether type, of formula: $R(OCH_2CH_2)_nOCH_2COOH$ in which: R = octylphenyl n = average value of 4 sold under the name Akypo OP 40 by the Company Chem Y at 90% AS | 5.0 g AS |
| 30% AS Ammonium lauryl sulphate | 5.0 g AS |
| 38% AS Sodium α-olefinsulphonate | 5.0 g AS |
| Quaternised polymer sold at 60–63% AS concentration under the name Mirapol 175 by the Company Miranol | 1.0 g AS |
| Polysiloxane containing a hydroxy-acylamino functional group, sold under the name Q2-8413 by the Company Dow Corning | 2.0 g |
| Sodium chloride | 1.5 g |
| Triethanolamine | qs pH = 6.3 |
| Water | qs 100 g |

EXAMPLE 2

A shampoo of the following composition is prepared:

| | |
|---|---|
| Surface-active agent of the polyoxyethylenated carboxylic acid ether type, of formula: $R(OCH_2CH_2)_nOCH_2COOH$ in which: R = octylphenyl n = average value of 4 sold under the name Akypo OP 40 by the Company Chem Y at 90% AS | 5.0 g AS |
| 30% AS Ammonium lauryl sulphate | 5.0 g AS |
| 38% AS Sodium α-olefinsulphonate | 5.0 g AS |
| Copolymer of dimethyldiallyl-ammonium chloride and of acrylamide sold under the name Merquat 550 at 8% AS by the Company Merck | 0.5 g AS |
| Polysiloxane containing a hydroxy-acylamino functional group, sold under the name Q2-8413 by the Company Dow Corning | 2.0 g |
| Sodium chloride | 1.5 g |
| Triethanolamine | qs pH = 6.2 |
| Water | qs 100 g |

EXAMPLE 3

A shampoo of the following composition is prepared:

| | |
|---|---|
| Surface-active agent of the polyoxyethylenated carboxylic acid ether type, of formula: $R(OCH_2CH_2)_nOCH_2COOH$ in which: R = octylphenyl n = average value of 4 sold under the name Akypo OP 40 by the Company Chem Y at 90% AS | 5.0 g AS |
| 30% AS Ammonium lauryl sulphate | 5.0 g AS |
| 38% AS Sodium α-olefinsulphonate | 5.0 g AS |
| Polymer P1 | 1.0 g |
| Polysiloxane containing a hydroxy-acylamino functional group, sold under the name Q2-8413 by the Company Dow Corning | 2.0 g |
| Sodium chloride | 1.5 g |
| Triethanolamine | qs pH = 6.3 |
| Water | qs 100 g |

EXAMPLE 4

A shampoo of the following composition is prepared:

| | |
|---|---|
| Surface-active agent of the polyoxyethylenated carboxylic acid ether type, of formula: $R(OCH_2CH_2)_nOCH_2COOH$ in which: R = $C_{12}$–$C_{14}$ alkyl n = average value of 4.5 sold under the name Akypo RLM 45 by the Company Chem Y at 90% AS | 12.0 g AS |
| Cocoamphocarboxyglycinate sold at 38% AS concentration under the name Miranol C2M conc. by the Company Miranol | 4.0 g AS |
| Copolymer of dimethyldiallylammonium chloride and of acrylamide, sold under the name Merquat 550 at 8% AS by the Company Merck | 0.2 g AS |
| Polysiloxane containing a hydroxyacyl-amino functional group, sold under the name Q2-8413 by the Company Dow Corning | 4.0 g |
| Polyethylene glycol (550E) and propylene glycol dioleate derivative, sold under the name Antil 141 Liquide by the Company Goldschmidt | 2.0 g AS |
| Hydrochloric acid | qs pH = 7.7 |
| Water | qs 100 g |

EXAMPLE 5

A shampoo of the following composition is prepared:

| | |
|---|---|
| Surface-active agent of the polyoxyethylenated carboxylic acid ether type, of formula: $R(OCH_2CH_2)_nOCH_2COOH$ in which: R = ($C_{12}$–$C_{14}$) alkyl n = average value of 2.5 sold under the name Akypo RLM 25 by the Company Chem Y at 90% AS | 7.2 g AS |
| 30% AS Ammonium lauryl sulphate | 5.0 g AS |
| 38% AS Sodium α-olefinsulphonate | 5.0 g AS |
| Quaternised polymer sold at 60–63% AS concentration under the name Mirapol 175 by the Company Miranol | 0.5 g AS |
| Polysiloxane containing a hydroxyacyl-amino functional group, sold under the name Q2-8413 by the Company | 10.0 g |
| Dow Corning Polyethylene glycol (550E) and propylene glycol dioleate derivative, sold under the name Antil 141 Liquide by the Company Goldschmidt at 43.6% AS | 1.5 g AS |
| Copra acid diethanolamide | 2.5 g |
| Sodium chloride | 3.0 g |
| Sodium hydroxide | qs pH = 5.6 |
| Fragrance, preservatives | qs |
| Water | qs 100 g |

EXAMPLE 6

A shower gel of the following composition is prepared:

| | |
|---|---|
| ($C_{12}$–$C_{14}$/70–30) Lauryl sulphate of triethanolamine sold at 40% AS | 30.0 g AS |
| ($C_{12}$–$C_{18}$) Alkyl dimethylcarboxy-methylammonium hydroxide sold at 32% AS under the name Dehyton AB 30 by the Company Henkel | 3.2 g AS |
| Polysiloxane containing a hydroxyacyl-amino functional group, sold under the name Q2-8413 by the Company Dow Corning | 1.5 g |
| Copra monoisopropanolamide | 2.5 g |
| ($C_{16}$–$C_{18}$/70–30)Ethylene glycol distearate | 2.0 g |
| Polymer of hydroxyethyl cellulose and of epichlorohydrin quaternised with trimethylamine, sold under the name JR 400 by the Company Union Carbide | 0.5 g |
| Sodium chloride | 2.0 g |
| Triethanolamine | qs ph = 7 |
| Fragrance, preservatives | qs |
| Water | qs 100 g |

We claim:

1. A composition for washing or conditioning keratinous materials, comprising (a) 0.1 to 20% by weight of a silicone containing a hydroxyacylamino functional group chosen from the compounds corresponding to the formula:

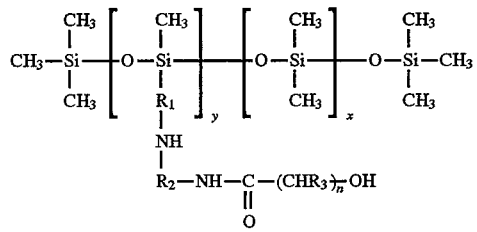

in which:

$R_1$ and $R_2$ denote $(CH_2)_2$, $(CH_2)_3$, $(CH_2)_4$, or —$CH_2CH(CH_3)CH_2$—;

$R_3$ denotes hydrogen, hydroxyl, alkyl or hydroxyalkyl;

n is an integer varying from 2 to 7;

x is an integer varying from 20 to approximately 1,500;

y varies between approximately 0.5 and 10;

and the y/x ratio is less than 0.05;

(b) 0.05 to 8% by weight of a substantive polymer wherein the substantive polymer consists of units which correspond to the formula:

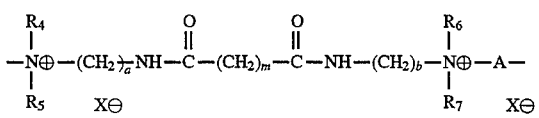

in which:

R$_4$, R$_5$, R$_6$ and R$_7$ represent a substituent selected from the group consisting of a hydrogen atom, a methyl group, an ethyl group, a propyl group, a β-hydroxyethyl group and a —CH$_2$CH$_2$(OCH$_2$CH$_2$)$_p$OH radical, and wherein R$_4$, R$_5$, R$_6$ and R$_7$ do not simultaneously represent a hydrogen atom, wherein p is 0 to 6, wherein a and b are 1 to 6, m is 0 to 34, X$\ominus$ is a halogen atom, and A is a divalent radical; and (c) an effective amount of at least one detergent surface-active agent which is selected from a group of agents consisting of (i) anionic surface-active agents selected from the group consisting of alkali metal salts, ammonium salts, amine salts, aminoalcohol salts of alkyl ether sulphates, alkylamidoether sulphates, alkylarylpolyether sulphates, and monoglyceride sulphates; magnesium salts of alkyl ether sulphates, alkylamidoether sulphates, alkylarylpolyether sulphates, and monoglyceride sulphates; alkylsulphonates, alkylamidesulphonates, alkylarylsulphonates, olefinsulphonates, paraffinsulphonates, alkylsulphosuccinates, alkylethersulphosuccinates, alkylamidesulphosuccinates, alkylsulphosuccinamates, alkylsulphoacetates, alkyl ether phosphates, acylsarcosinates, N-acyltaurates, fatty acid salts, acids of copra oil, acids of hydrogenated copra oil, and acyl lactylates wherein the acyl radical contains from 8 to 20 carbon atoms;

(ii) amphoteric agents;

(iii) zwitterionic agents;

(iv) non-ionic surface active agents selected from the group consisting of polyethoxylated fatty acids with a fatty chain containing 8 to 18 carbon atoms, polypropoxylated fatty acids with a fatty chain containing 8 to 18 carbon atoms, polyglycerolated fatty acids with a fatty chain containing 8 to 18 carbon atoms, alcohols with a fatty chain containing 8 to 18 carbon atoms, α-diols with a fatty chain containing 8 to 18 carbon atoms, alkylphenols with a fatty chain containing 8 to 18 carbon atoms, copolymers of ethylene oxide and propylene oxide, condensates of ethylene oxide with fatty alcohols, condensates of propylene oxide with fatty alcohols, polyethoxylated fatty amides, polyglycerolated fatty amides, polyethoxylated fatty amines, oxyethylenated fatty acid esters of sorbitan, fatty acid esters of sucrose, fatty acid esters of polyethylene glycol, fatty acids esters of glycols, alkylpolyglycosides, oxides of (C$_{10}$–C$_{14}$) alkylamines, oxides of N-acylamidopropylmorpholine and amine oxides; and (v) mixtures thereof, in an aqueous medium, wherein said composition does not contain an alcohol suspending agent having 27 to 44 carbon atoms and one to two functional groups selected from the group consisting of an ether group, a thioether group and a sulphoxide group.

2. Composition according to claim 1, wherein the silicone containing a hydroxyacylamino functional group is a silicone corresponding to the formula:

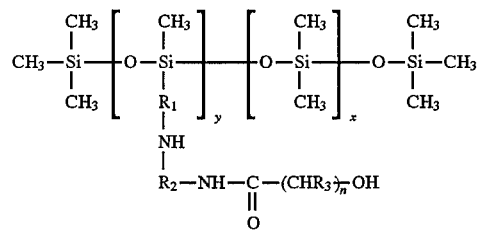

in which:

R$_1$ denotes —CH$_2$CH(CH$_3$)CH$_2$;

R$_2$ denotes —(CH$_2$)$_2$—;

R$_3$ denotes hydrogen;

x is equal to 392;

y is equal to 8;

n is equal to 3.

3. Composition according to claim 1 or claim 2, wherein the substantive polymer has a molecular weight of between 500 and approximately 5,000,000.

4. Composition according to claim 1, wherein the silicones containing a hydroxyacylamino functional group are present in amounts of between 0.5 and 10% by weight.

5. Composition according to claim 1, wherein the substantive polymers are present in amounts of between 0.1 and 5% by weight of the total composition.

6. Composition according to claim 1, wherein the detergent surface-active agents are present in amounts of between 5 and 50% by weight in relation to the total weight of the composition.

7. Composition according to claim 6, wherein the detergent surface-active agents are present in amount of between 8 and 35% by weight of the total composition.

8. Composition according to claim 1, further comprising a suspending agent for the silicones wherein the suspending agent is chosen from among:

a) the compounds of formula:

in which R$_{22}$ is an aliphatic radical containing a long carbon chain and X is a carboxylic, sulphuric or phosphoric acid residue or a radical derived from a carboxylic acid or from an amide; these compounds of formula R$_{22}$X are chosen from those in which:

(i) R$_{22}$ is a C$_{11}$–C$_{21}$ alkyl or alkenyl radical and X is:

a group COOD where D is a mono- or polyhydroxyalkyl radical derived from a c$_2$–c$_3$ polyol, a group CO(OCH$_2$CH$_2$)$_n$-OH where n has a value of between 2 and 150, a group

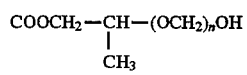

where n has a value of between 2 and 150, it being possible to esterify the free OM functional groups of the groups defined above with an acid R$_{22}$COOH where R$_{22}$ is a C$_{11}$–C$_{21}$ alkyl or alkenyl, a group CONR$_{23}$R$_{24}$ where R$_{23}$ and R$_{24}$ represent hydrogen or C$_1$–C$_4$ hydroxyalkyl, one at least representing C$_1$–C$_4$ hydroxyalkyl, a group ⅓ PO$_4^3$ M$_3$ where M represents an alkali metal, ammonium or a C$_1$–C$_4$ alkanolamine residue;

(ii) $R_{22}$ denotes a radical $R_{25}(OC_2H_4)_lOCH_2$ and X denotes a group COOM where M has the meaning shown above, $R_{25}$ denoting a $C_{12}$–$C_{14}$ alkyl radical and l an integer or decimal number of between 2.5 and 10, or else $R_{25}$ denotes oleyl and l varies from 2 to 9 or again $R_{25}$ denotes $(C_8$–$C_9)$ alkylphenyl and l varies from 4 to 8, or the derivatives in which $R_{22}$ denotes a $(C_{12}$–$C_{16})$ alkyl ether group and X a group $CONR_{23}R_{24}$, in which $R_{23}$ and $R_{24}$ have the same meaning as that shown above.

9. Composition according to claim 8 wherein the suspending agents are present in amounts of between 0.1 and 20% by weight of the total composition.

10. Composition according to claim 8 wherein the suspending agents are present in amounts between 0.5 and 10% by weight in relation to the total weight of the composition.

11. Composition according to claim 1, wherein the aqueous medium consists solely of water or of a mixture of water and a solvent.

12. Composition according to claim 1, wherein the composition further comprises an adjuvant chosen from pearlescence or opacifying agents in amounts up to 3%, and viscosity regulating agents in amounts up to 10% by weight in relation to the total weight of the composition.

13. Process for washing keratinous materials, comprising applying at least one composition as defined in claim 1 to keratinous materials, leaving the composition in contact with the keratinous materials for an effective period of time, and rinsing with water.

14. Process for conditioning hair, comprising applying at least one composition according to claim 1 to the hair, and rinsing the hair.

15. A composition according to claim 3, wherein the substantive polymer has a molecular weight of between 1,000 to 3,000,000.

16. A composition according to claim 1, wherein A is $-CH_2-CH_2-O-CH_2-CH_2-$.

17. A composition according to claim 1 wherein p is 1 to 6, and m is 1 to 34.

18. A process for washing or conditioning keratinous materials, comprising contacting keratinous materials with the composition of claim 1.

* * * * *

UNITED STATES PATENT AND TRADEMARK OFFICE
CERTIFICATE OF CORRECTION

PATENT NO. : 5,627,148
DATED : May 6, 1997
INVENTOR(S) : Dubief et al.

It is certified that error appears in the above-identified patent and that said Letters Patent is hereby corrected as shown below:

Title page of patent, left column, [76] should read --[75]--;

Title page of patent, left column, under "[75]" insert --[73] Assignee: L'Oreal, Paris, France.--;

Title page, 2nd column, delete 2nd line under "FOREIGN PATENT DOCUMENTS";

Column 2, line 27, "denote $(CH_2)$" should read --denote $(CH_2)_2$--;

Column 5, line 34, "Jointly" should read --jointly--;

Column 8, line 55, "5 unit (C)" should read --unit (C)--;

Column 18, line 12, "to" should read --and--.

Signed and Sealed this

Twenty-fourth Day of November, 1998

BRUCE LEHMAN

Attest:

Attesting Officer

Commissioner of Patents and Trademarks